US012691149B2

(12) United States Patent
Liu et al.

(10) Patent No.: US 12,691,149 B2
(45) Date of Patent: Jul. 28, 2026

(54) USE OF *BIFIDOBACTERIUM LACTIS* BL-99 IN FIGHTING AGING AND IMPROVING INNATE IMMUNITY

(71) Applicants: Inner Mongolia Yili Industrial Group Co., Ltd., Hohhot City (CN); INNER MONGOLIA DAIRY TECH RES INSTITUTE CO LTD, Hohhot City (CN)

(72) Inventors: Wei-Hsien Liu, Hohhot City (CN); Wen Zhao, Hohhot City (CN); Wei-Lian Hung, Hohhot City (CN); Gisela Adrienne Weiss, Hohhot City (CN); Carolien Annika Van Loo-Bouwman, Hohhot City (CN)

(73) Assignees: Inner Mongolia Yili Industrial Group Co., Ltd., Hohhot City (CN); INNER MONGOLIA DAIRY TECH RES INSTITUTE CO LTD, Hohhot City (CN)

( * ) Notice: Subject to any disclaimer, the term of this patent is extended or adjusted under 35 U.S.C. 154(b) by 466 days.

(21) Appl. No.: 18/253,136

(22) PCT Filed: Jul. 13, 2021

(86) PCT No.: PCT/CN2021/105957
§ 371 (c)(1),
(2) Date: Jul. 18, 2023

(87) PCT Pub. No.: WO2022/100126
PCT Pub. Date: May 19, 2022

(65) Prior Publication Data
US 2023/0414680 A1    Dec. 28, 2023

(30) Foreign Application Priority Data
Nov. 16, 2020    (CN) .......................... 202011279611.6

(51) Int. Cl.
| | |
|---|---|
| *A61K 39/02* | (2006.01) |
| *A23L 33/135* | (2016.01) |
| *A61K 8/99* | (2017.01) |
| *A61K 35/745* | (2015.01) |
| *A61P 31/04* | (2006.01) |
| *A61Q 19/08* | (2006.01) |

(52) U.S. Cl.
CPC .......... *A61K 35/745* (2013.01); *A23L 33/135* (2016.08); *A61K 8/99* (2013.01); *A61P 31/04* (2018.01); *A61Q 19/08* (2013.01)

(58) Field of Classification Search
CPC ... A61K 35/745; A23L 33/135; A23C 9/1232; A23C 9/1234; A61Q 19/08; A61Q 17/005; A23V 2200/302
See application file for complete search history.

(56) References Cited

U.S. PATENT DOCUMENTS

2022/0401499 A1    12/2022  Hung et al.

FOREIGN PATENT DOCUMENTS

| | | |
|---|---|---|
| CN | 102845518 A | 1/2013 |
| CN | 102960599 A | 3/2013 |
| CN | 103503990 A | 1/2014 |
| CN | 103898018 A | 7/2014 |
| CN | 110893193 A | 3/2020 |
| CN | 110893194 A | 3/2020 |
| CN | 110959792 A | 4/2020 |
| CN | 110964655 A | 4/2020 |
| CN | 110964657 A | 4/2020 |
| CN | 112870232 A | 6/2021 |
| WO | 2020063531 A1 | 4/2020 |
| WO | 2020063553 A1 | 4/2020 |

OTHER PUBLICATIONS

Wang et al ("Fermented milk supplemented with probiotics and prebiotics can effectively alter the intestinal microbiota and immunity of host animals", J Dairy Sci., 2012, 95, pp. 4813-4822).*
Zhang et al (J. Immunol Res. Dec. 2019. Article ID 4659728, pp. 1-12).*
Hor et al (Dermatologica Sinica. 32(3): 141-147, Sep. 2014).*
Sikorska et al (Inter. J. Antimicrob. Agents. Dec. 2013. 42(6): 475-481).*
Extended European Search Report issued on Sep. 2, 2024 for counterpart European patent application No. 21890657.6, "Novel Use of Bifidobacterium Lactis BL-99 in Fighting Aging and Improving Innate Immunity".
International Search Report for Int'l Application No. PCT/CN2021/ 105957, "Novel Use of Bifidobacterium Lactis BL-99 in Fighting Aging and Improving Innate Immunity", Dated: Sep. 28, 2021, 11 pages (With English Translation).
Written Opinion for Int'l Application No. PCT/CN2021/105957, "Novel Use of Bifidobacterium Lactis BL-99 in Fighting Aging and Improving Innate Immunity", Dated: Sep. 28, 2021, 14 pages (With English Translation).
Zhao, W. et al., "Function Research of Heat-inactivated Bifidobacterium Lactis BL-99 in Ameliorating Colitis and Regulating Intestinal Microbiota in Mice," Dairy Industry, 7 pages (2020) (With English Abstract).

(Continued)

*Primary Examiner* — Jennifer E Graser
(74) *Attorney, Agent, or Firm* — Hamilton, Brook, Smith & Reynolds, P.C.

(57) ABSTRACT

The present disclosure provides novel uses of *Bifidobacterium lactis* BL-99 in anti-aging and improving innate immunity. The *Bifidobacterium lactis* strain according to the present disclosure has a deposit number of CGMCC 15650. It is discovered in the present disclosure that this strain alone has an anti-aging effect, is capable of improving innate immunity of an organism, and is capable of enhancing resistance of an organism to *Staphylococcus aureus* infection, thereby providing use of the *Bifidobacterium lactis* strain of deposit number CGMCC 15650 in preparation of a composition having an anti-aging effect, capable of improving innate immunity of an organism, and/or capable of enhancing resistance of an organism to *Staphylococcus aureus* infection.

11 Claims, 2 Drawing Sheets

(56) References Cited

OTHER PUBLICATIONS

Chinese Novelty Search Report for Chinese Appl. No. 202011279611.6, "Novel Use of Bifidobacterium Lactis BL-99 in Fighting Aging and Improving Innate Immunity", Dated: Apr. 22, 2021, 13 pages (With English Translation).

Chinese Search Report for Chinese Appl. No. 202011279611.6, "Novel Use of Bifidobacterium Lactis BL-99 in Fighting Aging and Improving Innate Immunity", Dated: Jul. 12, 2022, 5 pages (With English Translation).

Arunachalam, K. et al., Enhancement of natural immune function by dietary consumption of Bifidobacterium lactis (HN019), European Journal of Clinical Nutrition, 54: 263-267 (2000).

Jinggang, Lan and Hu Hong, "Anti-Aging Effect of Bifidobacteria," Chinese Journal of Microecology, 7(6): 8-11 (1995) (With English Abstract).

Liu, X. et al., "Research progress on classification, physiological function and application of Bifidobacterium," Biobusiness, No. 3, 6 pages (2017) (With English Abstract).

Miller, L.E. et al., "The Effect of *Bifidobacterium animalis* ssp. lactis HN019 on Cellular Immune Function in Healthy Elderly Subjects: Systematic Review and Meta-Analysis," Nutrients 2017, 9, 191, 9 pages (2017).

* cited by examiner

USE OF *BIFIDOBACTERIUM LACTIS* BL-99 IN FIGHTING AGING AND IMPROVING INNATE IMMUNITY

This application is the U.S. National Stage of International Application No. PCT/CN2021/105957, filed Jul. 13, 2021, which designates the U.S., published in Chinese, and claims priority under 35 U.S.C. § 119 or 365 (c) to Chinese Application No. 202011279611.6, filed Nov. 16, 2020. The entire teachings of the above applications are incorporated herein by reference.

FIELD OF THE INVENTION

The present disclosure relates to the field of microbial biotechnology, and in particular to a novel use of *Bifidobacterium lactis* BL-99 (deposit number CGMCC 15650) in preparation of a composition having an anti-aging effect, capable of improving innate immunity of an organism, and/or capable of enhancing resistance of an organism to *Staphylococcus aureus* infection.

BACKGROUND ART

Among various physiological functionalities in the body, the immune system is vulnerable to attacks. The immune system is in constant contact with most organs and cells in the body, and an change in it inevitably affects the tissue cells of these organs. With increasing age, the function of the immune system gradually declines, and both the innate immune response and acquired immune response decline accordingly, resulting in certain diseases that seriously affect tissues and organs, and accelerating aging of various systems in the body. Immunosenescence refers to a phenomenon of susceptibility to chronic and acute diseases due to dysregulation of immunological functions. The decline in immunological functions is one of the important factors causing aging of a body, so strengthening of immunological functions of the body can reduce pathological aging.

Probiotics are a type of single microorganism species or a well-defined mixture of microorganisms that benefit a host's health by changing the composition of the flora in a certain part of the host. The probiotic effect refers to a beneficial physiological effect to a host, produced by a microbial preparation or fermented product regulating the host's mucosal and systemic immunological functions and improving intestinal nutrition and flora balance. With the increase in the aging population, functional foods that can provide probiotic effects, control aging, and prolong life are of growing interest. HIROMI KIMOTO-NIRA et al. used SAMP6 in a senescence-accelerated mouse model (SAM), and found that the spleen cells of SAMP6 mice produced more IL-12 and IFN-γ after the mice took heat-inactivated *Lactococcus lactis* subsp. *cremoris* H61. The study suggests that the ability of *Lactococcus lactis* subsp. *cremoris* H61 to inhibit certain aging phenomena may be related to its immunomodulatory function.

*Caenorhabditis elegans* (*C. elegans*) is a common, free-living small soil nematode belonging to the subclass Rhabditia, order Rhabditidia, family Rhabditoidea. It feeds on bacteria and has a life cycle of approximately 3 days and an average lifespan of 3 weeks. It is worm-like, with an adult body length of about 1.0 to 1.5 mm and a body diameter of about 70.0 μm. *C. elegans* is bilaterally symmetrical, has a cuticular covering on the body surface, without segmentation, and has four main skin cords and a pseudopodial cavity filled with body fluid. The biological characteristics of *C.*

*elegans*, such as a simple structure, a transparent body, ease for observation, and a short reproductive cycle, make it suitable as a model organism. Studying the mechanisms of aging and lifespan control in nematodes and applying the results to other organisms are of great significance for extending human lifespan and improving the quality of human life. The experiment herein explores the anti-aging effect of probiotics in the model animal *C. elegans* by observing its lifespan, and provides a theory support for development and utilization of probiotic products that have an anti-aging effect and improve innate immunity.

SUMMARY OF THE INVENTION

An objective of the present disclosure is to provide novel use of *Bifidobacterium lactis* BL-99.

The present disclosure provides a *Bifidobacterium lactis* strain, named BL-99 in the present disclosure. The strain was deposited on Apr. 26, 2018 at the China General Microbiological Culture Collection Center (CGMCC) (Address: Institute of Microbiology, Chinese Academy of Sciences, No. 3, Yard 1, Beichen West Road, Chaoyang District, Beijing, China), under the classification name: *Bifidobacterium lactis*; deposit number: CGMCC 15650. The *Bifidobacterium lactis* strain provided by the present disclosure has gastric acid resistance and intestinal juice resistance, with a survival rate of more than 62% after 30 min treatment, and more than 61% after 2 h treatment in pH 2.5 gastric acid, and a survival rate of more than 70% after 2 h treatment in pH 6.8 small intestinal fluid. *Bifidobacterium lactis* BL-99 is a biological material that has been published in CN110964655A and is available to the public.

It is discovered in the present disclosure that *Bifidobacterium lactis* BL-99 has an anti-aging effect, can improve innate immunity of an organism, and/or can enhance resistance of an organism to *S. aureus* infection.

Thus, in one aspect, the present disclosure provides use of *Bifidobacterium lactis* in preparation of a composition having an anti-aging effect, capable of improving innate immunity of an organism, and/or capable of enhancing resistance of an organism to *Staphylococcus aureus* infection, wherein the *Bifidobacterium lactis* is *Bifidobacterium lactis* of deposit number CGMCC 15650.

According to specific embodiments of the present disclosure, the enhancement of resistance of an organism to *S. aureus* infection described in the present disclosure comprises: enhancing an individual's ability to prevent *S. aureus* infection, reducing the ability of *S. aureus* to infect an individual, and/or alleviating symptoms caused by *S. aureus* infection in an individual such as food poisoning, enteritis, pneumonia, skin infection, wound ulceration and/or meningitis.

According to specific embodiments of the present disclosure, the anti-aging effect in the use of the composition of the present disclosure comprises delaying the aging or even death caused by *S. aureus* infection.

According to specific embodiments of the present disclosure, the *Bifidobacterium lactis* is used in the present disclosure in a form of a solid or liquid bacterial preparation for preparing the composition.

According to specific embodiments of the present disclosure, the composition of the present disclosure may comprise a food composition, a feed composition, a cosmetic composition, or a pharmaceutical composition.

According to specific embodiments of the present disclosure, in the use of the composition of the present disclosure, the organism is an animal or a human. The composition according to the present disclosure can be administered to an animal or human. The composition may also comprise conventional components in the field to which it belongs. For example, for a pharmaceutical composition, a suitable amount of auxiliaries may be comprised, and the auxiliaries may be excipients, diluents, fillers and/or absorption enhancers, etc. For a food composition, the *Bifidobacterium lactis* according to the present disclosure may be prepared in accordance with food products containing *Bifidobacterium lactis* in the art, and the composition may be in different forms depending on the needs of subjects, for example powder, lozenges, granules, microcapsules and/or liquid formulations.

According to specific embodiments of the present disclosure, the composition according to the present disclosure is for use in relieving symptoms caused by *S. aureus* infection, such as food poisoning, enteritis, pneumonia, skin infections, wound ulcers and/or meningitis. For specific applications, the *Bifidobacterium lactis* is administered in an amount of $1.0\times10^3$ CFU to $1.0\times10^{12}$ CFU/day, preferably in an amount of $1.0\times10^7$ CFU to $1.0\times10^{11}$ CFU/day.

According to specific embodiments of the present disclosure, the composition according to the present disclosure is for use in anti-aging (including life extension). For specific applications, the *Bifidobacterium lactis* is administered in an amount of $1.0\times10^3$ CFU to $1.0\times10^{12}$ CFU/day, preferably in an amount of $1.0\times10^7$ CFU to $1.0\times10^{11}$ CFU/day.

According to specific embodiments of the present disclosure, the composition according to the present disclosure is for use in improving innate immunity. For specific applications, the *Bifidobacterium lactis* is administered in an amount of $1.0\times10^3$ CFU to $1.0\times10^{12}$ CFU/day, preferably in an amount of $1.0\times10^7$ CFU to $1.0\times10^{11}$ CFU/day.

In a specific embodiment of the present disclosure, the composition according to the present disclosure is a food composition, and the food is a fermented dairy product (e.g., fermented milk, flavored fermented milk, a fermented milk beverage, etc.), cheese, a milk-containing beverage, a solid beverage, or milk powder.

In another specific embodiment of the present disclosure, the composition according to the present disclosure is a pharmaceutical composition, and the pharmaceutical may be an oral preparation or a topical preparation, such as an ointment for application, etc.

In another specific embodiment of the present disclosure, the composition according to the present disclosure is a cosmetic product having an anti-aging effect, capable of improving innate immunity of an organism, and/or capable of enhancing resistance of an organism to *Staphylococcus aureus* infection.

In another aspect, the present disclosure also provides a method for anti-aging, improving innate immunity of an organism, and/or enhancing resistance of an organism to *S. aureus* infection, the method comprising:

administering an effective amount of *Bifidobacterium lactis* to an organism, wherein the *Bifidobacterium lactis* is *Bifidobacterium lactis* of deposit number CGMCC 15650.

According to specific embodiments of the present disclosure, the enhancement of resistance of an organism to *S. aureus* infection described in the present disclosure comprises: enhancing an individual's ability to prevent *S. aureus* infection, reducing the ability of *S. aureus* to infect an individual, and/or alleviating food poisoning, enteritis, pneumonia, skin infection, wound ulceration and/or meningitis caused by *S. aureus* infection in an individual.

According to specific embodiments of the present disclosure, in the present disclosure, the *Bifidobacterium lactis* is administered in an amount of $1.0\times10^3$ CFU to $1.0\times10^{12}$ CFU/day.

According to specific embodiments of the present disclosure, in the present disclosure, the *Bifidobacterium lactis* is preferably administered in an amount of $1.0\times10^7$ CFU to $1.0\times10^{11}$ CFU/day.

In summary, the present disclosure provides novel uses of *Bifidobacterium lactis* BL-99, which has an anti-aging effect, is capable of improving innate immunity of an organism, and/or is capable of enhancing resistance of an organism to *Staphylococcus aureus* infection, and can be used in preparation of food, drugs, cosmetics and feed having an anti-aging effect and an innate immunity-improving effect, and may find wide applications.

DETAILED DESCRIPTION OF THE INVENTION

Figure 1:
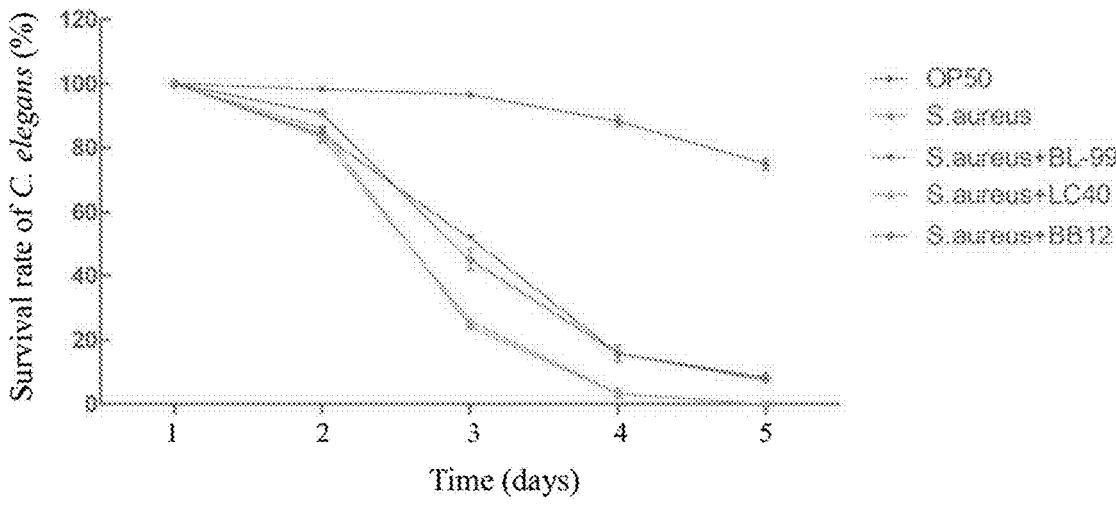
FIG. 1 shows the pathogenicity of *S. aureus* on *C. elegans* and the effect of addition of probiotic strains; for each group indicated in the figure, the intervening substance (probiotic) added in the infection stage was the same as that in the culture stage.

In order to allow a clearer understanding of the technical features, purposes and beneficial effects of the present disclosure, the technical solutions of the present disclosure will be described in detail below in conjunction with specific examples. It should be understood that these examples are only used to illustrate the present disclosure, and are not intended to limit the scope of the present disclosure. In the examples, the starting reagents and materials are commercially available, and the experimental methods, where no specific conditions are indicated, are conventional methods and conditions well known in the art, or are performed as recommended by the instrument manufacturer.

Example 1: Assay of the Anti-Aging Effect of Probiotics on *C. elegans*

1.1 Materials and Instrument

*Bifidobacterium lactis* BL-99 was obtained from Inner Mongolia Yili Industrial Group Co., Ltd.; *Bifidobacterium animalis* subsp. *lactis* BB-12 was purchased from ChrHansen; *Lactobacillus fermentum* LC40 was purchased from Biosearch life; Wild-type *Caenorhabditis elegans* (*C. elegans*) was purchased from Biopolis SL Biotechnology Company, Spain; *S. aureus* ATCC25923 was purchased from Biopolis SL Biotechnology Company, Spain.

All other reagents used in the experiments were purchased from Sinopharm Chemical Reagent Co., Ltd. SPX-150B-Z biochemical incubator: Shanghai B oxun Industrial Co., Ltd. Medical Equipment Factory; Olympus microscope (OlympusBX41): Nanjing Ailon Instrument Co., Ltd.; LDZX-50KBS vertical autoclave: Shanghai Shen'an Medical Instrument Factory; T6 UV/Vis spectrophotometer: Beijing Persee General Instrument Co., Ltd.; Multiskan FC microplate reader: Thermo Fisher (Shanghai) Instrument Co., Ltd.

1.2 Experimental Method 1.2.1 Probiotic Activation

*Lactobacillus* was incubated and activated at 37° C. in an MRS medium. *Bifidobacterium lactis* were incubated and activated at 37° C. in an MRS+Cys medium. Cells were collected and eluted with saline, and adjusted to $1 \times 10^8$ CFU in an NGM medium for later use.

1.2.2 *C. elegans* Longevity Measurement

Nematodes at the same age were obtained and cultured in petri dishes containing nematode agar medium (nematode medium containing *E. coli* OP50 as food), which was further supplemented with different probiotic bacteria ($1 \times 10^8$ CFU) for co-culturing. After the nematodes grew to adult forms, they were transferred to petri dishes inoculated with *S. aureus* ATCC25923 at $10^8$ to $10^9$ CFU/mL, to simulate infection with *S. aureus*. For each group, the intervening substance (probiotic) added in the infection stage was the same as that in the culture stage. Two controls were used to respectively create the condition without pathogenic bacteria (nematode dishes containing *E. coli* OP50, i.e., the OP50 group), and the condition with pathogenic *S. aureus* infection and without any intervening material (dishes containing only *S. aureus*, i.e., the *S. aureus* group). Further groups wherein the intervening substance was added during the culture stage but not during the infection stage, and groups wherein the intervening substance was not added during the culturing stage but was added during the infection stage, were established.

After culturing the nematodes for a few days, their survival rate was counted on a daily basis. If the nematodes did not respond to a platinum wire, they were considered dead. Two independent assays were carried out for each condition.

A comparative statistical analysis of the survival curves was carried out, and the log rank survival significance analysis was carried out using the GraphPad Prism 4 statistical package. Differences in the effect on nematode survival between groups on each day were analyzed using Two-way ANOVA and then compared between groups by Tukey's post hoc test. Significant differences in survival rates between the groups were analyzed using one-way ANOVA and Dunnett's post hoc test.

1.2.3 Experimental Results

Longevity was the most straightforward reflection of a change in *C. elegans* before and after the exposure.

As shown in FIG. 1, the survival rate of the *S. aureus*-infected *C. elegans* decreased significantly from day 3 and all *C. elegans* died by day 5. In contrast, the survival rate of the *C. elegans* group treated with $10^8$ CFU *Bifidobacterium lactis* BL-99 was 51.7% on day 3 and $7.5 \pm 0.7\%$ on day 5, which was significantly different from that of the *S. aureus* group (p<0.001). The survival rate of the *C. elegans* group treated with *Lactobacillus fermentum* LC 40 was $25.85 \pm 0.85\%$ on day 3 and 0% on day 5, which was not significantly different from the *S. aureus* group.

Figure 2:
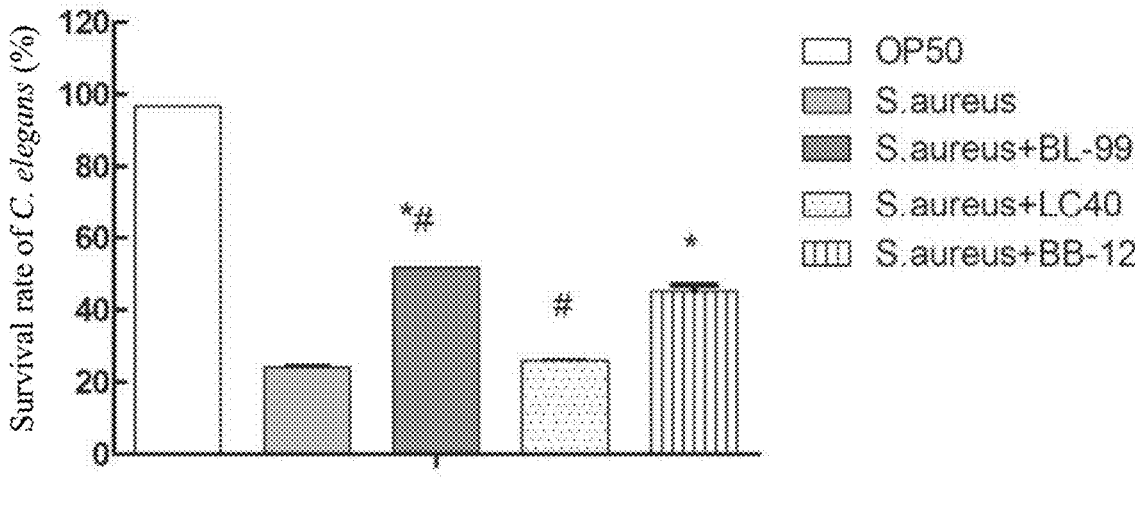
FIG. 2 shows the survival rate of *C. elegans* after 3 days of intervention with *S. aureus* and probiotics; for each group indicated in the figure, the intervening substance (probiotic) added in the infection stage was the same as that in the culture stage.

As shown in FIG. 2, *Bifidobacterium lactis* BL-99 was able to significantly extend the life span of *C. elegans* as compared to *Lactobacillus fermentum* LC40 (p<0.001).

In addition, experiments of the present disclosure showed that the survival rate of *C. elegans* in the group with *Bifidobacterium lactis* BL-99 intervention in the culture stage and without any intervention in the infection stage was significantly higher than that in the group without any intervention in either the culture stage or the infection stage.

Example 2: Analysis of Antibacterial Characteristics of Probiotics Against *S. aureus*

The antibacterial activity of probiotic bacteria against *S. aureus* was analyzed using the paper diffusion method. 1 mL of bacterial suspension at a concentration of $1 \times 10^8$ CFU/mL was pipetted into 15 mL RCA medium (50° C.), mixed well and poured into a dish. After the agar surface was solidified, drug susceptibility paper was attached to the agar surface with 3 pieces of the same drug susceptibility paper attached at even and moderate intervals on each petri dish, and the dishes were allowed to stand for 5 min and then turned over, and cultured at a constant temperature of 37° C. under a microaerobic condition. After 48 h, the diameter of the inhibition zone was measured and recorded.

Figure 3:
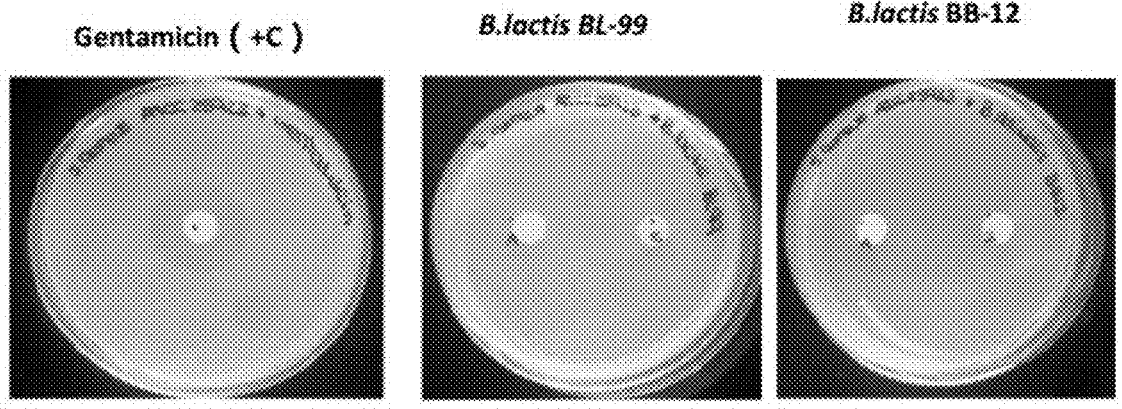
FIG. 3 shows the antibacterial effect of probiotics on *S. aureus*.

In order to analyze whether the life extension effect of probiotics on *C. elegans* is due to an antibacterial ability, the antibacterial ability of the probiotic strains was further evaluated by the paper diffusion method. The results showed that none of the probiotics produced transparent circles in the dishes, indicating that the probiotic strains used in the present disclosure had no antibacterial effect on *S. aureus* (FIG. 3). The probiotics do not exert the anti-aging effect and the effect of improving innate immunity on *C. elegans* by inhibiting *S. aureus*.

The above results demonstrate that *Bifidobacterium lactis* BL-99 (deposit number: CGMCC 15650) has a good potential in anti-aging and improving innate immunity, and can be used in food, such as fermented milk, cheese, milk-containing beverages, milk powder or any other food products containing this strain or its derivatives.

The invention claimed is:

1. A method for anti-immune aging, and/or enhancing resistance of an organism to *Staphylococcus aureus* infection to improve innate immunity of an organism, wherein the organism is an animal or a human, the method comprising:

administering an effective amount of a *Bifidobacterium lactis* strain to an organism, wherein the *Bifidobacterium lactis* strain is *Bifidobacterium lactis* of deposit number CGMCC 15650.

2. The method according to claim 1, wherein the enhancing resistance of an organism to *Staphylococcus aureus* infection comprises: enhancing an individual's ability to prevent *Staphylococcus aureus* infection, and/or alleviating food poisoning, enteritis, pneumonia, skin infection, wound ulceration and/or meningitis caused by *Staphylococcus aureus* infection in an individual.

3. The method according to claim 1, wherein the *Bifidobacterium lactis* strain is administered in an amount of $1.0 \times 10^3$ CFU to $1.0 \times 10^{12}$ CFU per day.

4. The method according to claim 1, wherein the *Bifidobacterium lactis* strain is used in a form of a solid or liquid bacterial preparation for preparing a composition; the composition comprises a food composition, a feed composition, a cosmetic composition, or a pharmaceutical composition.

5. The method according to claim 4, wherein the pharmaceutical composition further comprises a pharmaceutically acceptable auxiliary comprising an excipient, a diluent, a filler and/or an absorption enhancer.

6. The method according to claim 4, wherein the food composition comprises powder, lozenges, granules, microcapsules, or liquid formulations.

7. The method according to claim 1, wherein the *Bifidobacterium lactis* strain is for use in relieving food poisoning, enteritis, pneumonia, skin infection, wound ulceration and/or meningitis caused by *Staphylococcus aureus* infection;

wherein the *Bifidobacterium lactis* strain is administered in an amount of $1.0 \times 10^3$ CFU to $1.0 \times 10^{12}$ CFU per day.

8. The method according to claim 1, wherein the *Bifidobacterium lactis* strain is used in a form of a food composition.

9. The method according to claim 8, wherein the food is a fermented dairy product, cheese, a milk-containing beverage, a solid beverage, or milk powder.

10. The method according to claim 1, wherein the *Bifidobacterium lactis* strain is administered in an amount of $1.0 \times 10^7$ CFU to $1.0 \times 10^{11}$ CFU per day.

11. The method according to claim 1, wherein the *Bifidobacterium lactis* strain is for use in relieving food poisoning, enteritis, pneumonia, skin infection, wound ulceration and/or meningitis caused by *Staphylococcus aureus* infection;

wherein the *Bifidobacterium lactis* strain is administered in an amount of $1.0 \times 10^7$ CFU to $1.0 \times 10^{11}$ CFU per day.

\* \* \* \* \*